United States Patent [19]
Menard et al.

[11] Patent Number: 5,810,797
[45] Date of Patent: Sep. 22, 1998

[54] DISPOSABLE DIAPER HAVING A HUMIDITY TRANSFER AREA

[75] Inventors: Karen Marie Menard, Neenah; Thomas Walter Odorzynski, Green Bay; Joel Scott Sherman, Neenah, all of Wis.

[73] Assignee: Kimberly-Clark Worldwide, Inc., Neenah, Wis.

[21] Appl. No.: 639,655

[22] Filed: Apr. 29, 1996

Related U.S. Application Data

[62] Division of Ser. No. 344,429, Nov. 23, 1994, Pat. No. 5,558,658.

[51] Int. Cl.$^6$ .................................................. A61F 13/15
[52] U.S. Cl. ..................... 604/378; 604/358; 604/385.1
[58] Field of Search ................................ 604/358, 385.1, 604/383, 382, 378

[56] References Cited

U.S. PATENT DOCUMENTS

| | | |
|---|---|---|
| 1,353,750 | 9/1920 | Heitler . |
| 2,544,069 | 3/1951 | Cutler . |
| 2,796,064 | 6/1957 | Green et al. . |
| 2,880,727 | 4/1959 | Whalen . |
| 3,081,772 | 3/1963 | Brooks et al. . |
| 3,150,665 | 9/1964 | May, Jr. et al. . |
| 3,989,867 | 11/1976 | Sisson . |
| 4,341,216 | 7/1982 | Obenour ................................. 128/287 |
| 4,609,584 | 9/1986 | Cutler et al. ............................. 428/156 |
| 4,626,252 | 12/1986 | Nishizawa et al. ...................... 604/370 |
| 4,681,793 | 7/1987 | Linman et al. .......................... 428/138 |
| 4,699,733 | 10/1987 | Matsumura et al. ..................... 282/521 |
| 4,798,603 | 1/1989 | Meyer et al. . |
| 4,824,718 | 4/1989 | Hwang ..................................... 428/284 |
| 4,861,652 | 8/1989 | Lippert et al. . |
| 4,902,553 | 2/1990 | Hwand et al. ........................... 428/156 |
| 4,916,005 | 4/1990 | Lippert et al. . |
| 4,988,344 | 1/1991 | Reising et al. .......................... 604/368 |
| 5,085,654 | 2/1992 | Buell . |
| 5,137,525 | 8/1992 | Glassman . |
| 5,171,239 | 12/1992 | Igaue et al. . |
| 5,176,668 | 1/1993 | Bernardin . |
| 5,176,672 | 1/1993 | Breummer et al. . |
| 5,188,626 | 2/1993 | Toyoda et al. . |
| 5,192,606 | 3/1993 | Proxmire et al. . |
| 5,196,000 | 3/1993 | Clear et al. . |
| 5,221,274 | 6/1993 | Buell et al. . |
| 5,234,423 | 8/1993 | Alemany et al. . |
| 5,242,436 | 9/1993 | Weil et al. . |
| 5,331,015 | 7/1994 | DesMarais et al. . |
| 5,401,267 | 3/1995 | Couture-Dorschner et al. . |
| 5,509,915 | 4/1996 | Hansen et al. . |
| 5,527,302 | 6/1996 | Endres et al. ......................... 604/385.1 |
| 5,549,775 | 8/1996 | Odorzynski . |
| 5,558,658 | 9/1996 | Menard et al. . |
| B1 4,636,207 | 11/1989 | Buell . |

FOREIGN PATENT DOCUMENTS

| | | |
|---|---|---|
| 0422504A2 | 4/1971 | European Pat. Off. . |
| 0 336 578 A1 | 10/1989 | European Pat. Off. . |
| 0 343 941 A2 | 11/1989 | European Pat. Off. . |
| 0422504 b1 | 4/1991 | European Pat. Off. . |
| 0 477 802 A1 | 4/1992 | European Pat. Off. . |
| 2 705 029 A1 | 11/1994 | France . |

*Primary Examiner*—John G. Weiss
*Assistant Examiner*—Dennis Ruhl

[57] ABSTRACT

An absorbent article which delimits a front waistband section, a rear waistband section and an intermediate section which interconnects the front and rear waistband sections. The article includes a substantially fluid-impermeable backsheet layer, a liquid-permeable topsheet layer positioned in facing relation with the backsheet layer, and an absorbent body located between the backsheet layer and topsheet layer. The article further defines a humidity transfer area in at least one of the waistband sections. A humidity transfer material overlays the humidity transfer area.

33 Claims, 5 Drawing Sheets

DISPOSABLE DIAPER HAVING A HUMIDITY TRANSFER AREA

CROSS-REFERENCE TO RELATED APPLICATION

This is a division of application Ser. No. 344,429, filed Nov. 23, 1994, now U.S. Pat. No. 5,558,658, the disclosure of which is incorporated by reference.

FIELD OF THE INVENTION

The present invention relates to an absorbent article for absorbing body fluids and exudates, such as urine. More particularly, the present invention relates to absorbent garments, such as disposable diapers and adult incontinence garments, which are configured to absorb body exudates while also helping to provide reduced skin hydration.

BACKGROUND OF THE INVENTION

Many known diaper configurations employ absorbent materials located between a liquid-pervious topsheet and a vapor- and liquid-impermeable backsheet. Such backsheets are well suited to prevent the migration of liquid waste from the absorbent materials to the outer garments of a wearer. Unfortunately, the use of liquid- and vapor-impermeable backsheets can result in a relatively high degree of humidity within the diaper when in use. This may result in relatively high skin hydration levels and may lead to the onset of diaper rash.

In order to reduce the humidity level within diapers, breathable polymer films have been employed as outer covers for absorbent garments, such as disposable diapers. The breathable films are typically constructed with micropores to provide desired levels of liquid impermeability and vapor permeability. Other disposable diaper designs have been arranged to provide some level of breathability at the leg cuff regions of the diaper. Still other disposable diaper designs have been arranged to provide humidity transfer regions in the form of breathable panels in otherwise vapor-impermeable backsheets or to employ perforated regions to help ventilate the garment.

Disposable absorbent articles have also employed various additional layers between a topsheet layer and an absorbent layer. The additional layers are sometimes said to serve as an isolating layer to separate the skin of a wearer from the moisture contained in the absorbent materials of the diaper.

Conventional absorbent articles, such as those described above, have not been completely satisfactory. For example, articles which employ a microporous outer cover can exhibit a cold and clammy feeling when the garment is wetted and moisture is evaporating through the microporous film. The articles which employ perforated films or breathable panels can exhibit excessive leakage of liquids from the article and can excessively soil the wearer's outer garments. In addition, when the absorbent material of the article becomes loaded with liquid, the wet absorbent can block the escape of moisture from the wearer's skin. Other absorbent garment designs, which include additional layers between the topsheet layer and the absorbent materials, have not been able to sufficiently reduce the hydration of the wearer's skin. As a result, the wearer's skin has remained susceptible to abrasion and irritation.

SUMMARY OF THE INVENTION

In one aspect, the present invention relates to an absorbent article which generally delimits a front waistband section, a rear waistband section, and an intermediate section which interconnects said front and rear waistband sections. The article comprises a vapor-permeable backsheet having a length and a water vapor transmission rate value of at least about 1000 grams per square meter per 24 hours (g/sq.m/24 hr.), a liquid-permeable topsheet layer positioned in facing relation with the backsheet layer, and an absorbent body located between the backsheet layer and said topsheet layer, and having a length which is less than the length of said backsheet layer. The absorbent body overlays at least a portion of said backsheet layer. The article further comprises a humidity transfer area formed by positioning the absorbent body such that an area of at least about 5.0 square centimeters of said backsheet, in at least one waistband section of said article, is not overlaid by the absorbent body. The article further includes a humidity transfer material located between the topsheet layer and the backsheet layer and having a wet compression recovery value of at least about 74 percent. The humidity transfer material overlays the humidity transfer area and extends over the absorbent body and into the intermediate section of the article.

In a second embodiment, the present invention relates to an absorbent article which generally delimits a front waistband section, a rear waistband section, and an intermediate section which interconnects the front and rear waistband sections. The article comprises a substantially vapor-impermeable backsheet layer having a length, a liquid-permeable topsheet layer positioned in facing relation with the backsheet layer, and an absorbent body located between the backsheet layer and the topsheet layer, and having a length which is less than the length of the backsheet layer. The absorbent body overlays at least a portion of the backsheet layer. The article further includes a humidity transfer area formed by positioning the absorbent body such that an area of at least about 5.0 square centimeters of the backsheet, in at least one waistband section of the article, is not overlaid by the absorbent body and forming a vapor-permeable panel in said area of said backsheet which vapor-permeable panel is substantially liquid impermeable, has a water vapor transmission rate value of at least about 2500 grams per square meter per 24 hours, and an area of at least about 5.0 square centimeters. The garment also includes a humidity transfer material located between the topsheet layer and the backsheet layer. The humidity transfer material has a wet compression recovery value of at least about 74 percent, overlays said humidity transfer area, and extends over the absorbent body into the intermediate section of the article.

BRIEF DESCRIPTION OF THE DRAWINGS

The invention will be more fully understood and further advantages will become apparent when reference is made to the following detailed description of the invention and the accompanying drawings, in which.

DETAILED DESCRIPTION OF THE INVENTION

The following detailed description will be made in the context of a disposable diaper article. It is readily apparent, however, that the absorbent structure of the present invention would also be suitable for other absorbent articles, such as feminine care pads, incontinence garments, training pants, and the like.

Figure 1:
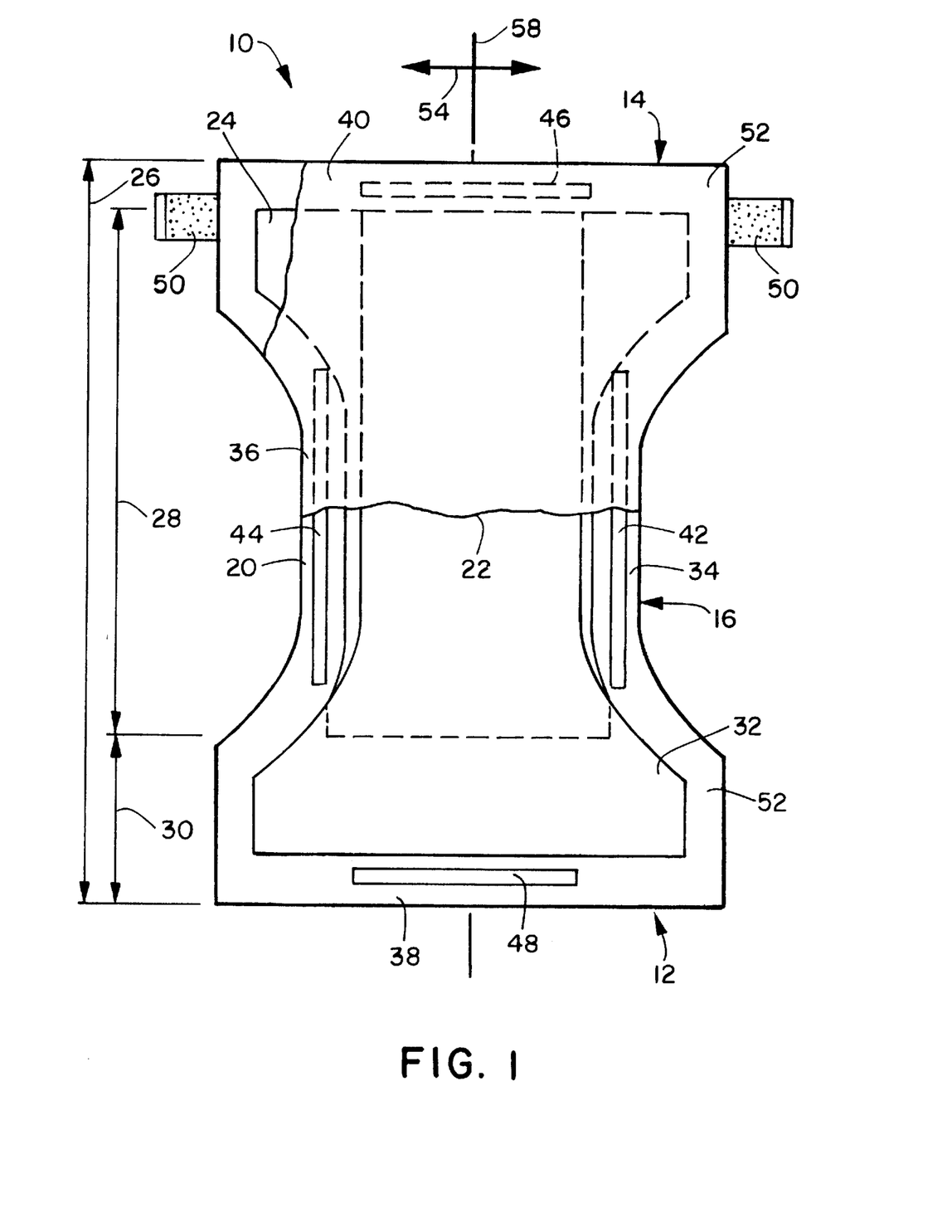
FIG. 1 representatively shows a partially cutaway, top plan view of an absorbent article according to one embodiment of the invention.

With reference to FIG. 1, an integral absorbent garment article, such as disposable diaper 10, generally delimits a front waistband section 12, a rear waistband section 14, and an intermediate section 16 which interconnects the front and rear waistband sections. The front and rear waistband sections include the general portions of the article which are constructed to extend substantially over the wearer's front and rear abdominal regions, respectively, during use. The intermediate section of the article includes the general portion of the article which is constructed to extend through the wearer's crotch region between the legs. The absorbent article further comprises a substantially liquid-impermeable, vapor-permeable backsheet layer 20, a liquid-permeable topsheet layer 22 positioned in facing relation with backsheet layer 20, and an absorbent body 24, such as an absorbent pad, is located between the backsheet layer and topsheet layer. The absorbent body 24 overlays at least a portion of the backsheet layer 20. The backsheet layer 20 has a length 26 which, in the illustrated embodiment, coincides with the length of the diaper 10. The absorbent body has a length 28 which is less than the length 26 of the backsheet layer. A humidity transfer area 30 is formed by positioning the absorbent body 24 such that an area of at least about 5.0 square centimeters, alternatively of at least about 22.0 square centimeters, alternatively of from about 45.0 to about 90.0 square centimeters, alternatively of about 58.0 square centimeters of the backsheet 20 in the front waistband section 12 is not overlaid by the absorbent body.

A humidity transfer material 32 is located between the topsheet layer 22 and the backsheet layer 20. The humidity transfer material 32 has a wet compression recovery of at least about 74 percent, overlays at least a portion of the humidity transfer area 30, and extends over the absorbent body 24 and into the intermediate section 16 of the diaper 10.

Marginal portions of diaper 10, such as marginal sections of backsheet 20, may extend past the terminal edges of absorbent body 24 and humidity transfer material 32. In the illustrated embodiment, for example, backsheet 20 extends outwardly beyond the terminal marginal edges of absorbent body 24 and humidity transfer material 32 to form side margins 34 and 36 and end margins 38 and 40 of the diaper. Topsheet 22 is generally coextensive with backsheet 20 but may optionally cover an area which is larger or smaller than the area of backsheet 20, as desired.

Diaper 10 may be of various suitable shapes. For example, the diaper may have an overall rectangular shape, T-shape or an approximately hour-glass shape. In the shown embodiment, diaper 10 has a generally I-shape.

The various components of diaper 10 are integrally assembled together employing various types of suitable attachment means, such as adhesive, sonic bonds, thermal bonds or combinations thereof. In the shown embodiment, for example, topsheet 22 and backsheet 20 are assembled to each other and to absorbent body 24 with lines of adhesive, such as a hot melt, pressure-sensitive adhesive. Similarly, other diaper components, such as elastic members 42, 44, 46 and 48, and fastening members 50, may be assembled into the diaper article by employing the above-identified attachment mechanisms.

The illustrated embodiment of diaper 10 includes ear portions 52 which extend laterally along the diaper cross-direction 54 and are positioned at least at the rear waistband section 14 of diaper 10. Ear portions 52 may also be located at front waistband section 12 of the diaper. The ear portions may be integral with backsheet layer 20 or may comprise separate sections which are composed of the same or different material than backsheet 20 and are suitably assembled and attached to the backsheet layer 20. Ear portions typically provide extensions of the diaper waistband suitable for completely encircling the waist of the wearer during use.

Fastening means, such as adhesive tapes 50, are employed to secure the diaper on a wearer. Alternatively, other fastening means, such as buttons, pins, snaps, hook-and-loop fasteners, mushroom-and-loop fasteners, or the like, may be employed.

Figure 2:
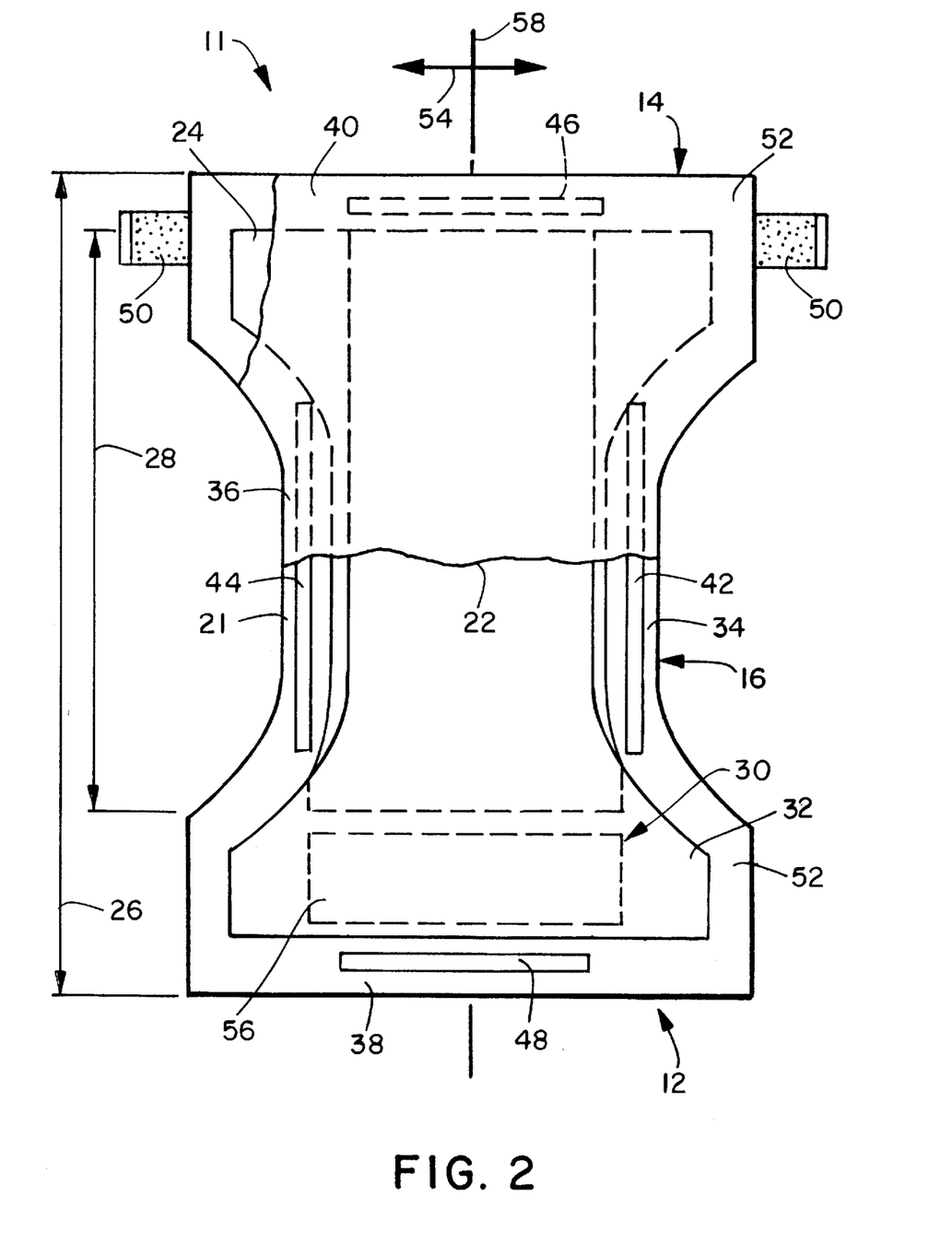
FIG. 2 representatively shows a partially cutaway, top plan view of an absorbent article according to a second embodiment of the invention.

To provide improved fit and to help reduce leakage of body exudates from diaper 10, the diaper side margins and end margins way be elasticized with suitable elastic members, such as single or multiple strands of elastic. The elastic strands may be composed of natural or synthetic rubber and may optionally be heat shrinkable or heat elasticizable. Elastic members 42 and 44 are constructed to operably gather and shirr side margins 34 and 36 to provide elasticized leg bands which can closely fit around the legs of the wearer to reduce leakage and provide improved comfort and appearance. Similarly, waist elastic members 46 and 48 can be employed to elasticize diaper end margins 38 and 40 to provide elasticized waistbands. The waist elastics are configured to operably gather and shirr the waistband sections to provide a resilient, comfortably close fit around the waist of the wearer. In FIG. 1 and 2, the elastic members are illustrated in their uncontracted, stretched condition for the purpose of clarity.

FIG. 2 illustrates a second embodiment of the present invention. The diaper 11 illustrated in FIG. 2 is identical to the diaper illustrated in FIG. 1 with the following exceptions. The vapor-permeable backsheet 20 of diaper 10 is replaced with a substantially liquid-impermeable, substantially vapor-impermeable backsheet layer 21. The humidity transfer area 30 is formed by positioning the absorbent body 24 such that an area of at least about 5.0 square centimeters of said backsheet 21 in the front waistband section 12 is not overlaid by the absorbent body 24 and by forming a vapor-permeable panel 56 in the backsheet layer 21. The vapor-permeable panel 56 is substantially liquid impermeable, has a water vapor transmission rate value of at least about 2500 g/sq.m/24 hr. and has an area of at least about 5.0 square centimeters. Vapor-permeable panel 56 is operably connected to backsheet layer 21 to extend partially or completely over at least one waistband section of diaper 11. The vapor-permeable panel 56 may be an integral portion of the backsheet or may be a separate component which is assembled to the backsheet. Vapor-permeable panel 56 is, for example, composed of a material having a water vapor transmission rate of at least about 2500 g/sq.m/24 hour. Diaper 11 is, otherwise, the same as diaper 10 with like numerals representing like elements.

Backsheet layer 20 is composed of a substantially liquid-impermeable material which is substantially permeable to vapor. In particular, the backsheet 20 is substantially permeable to at least water vapor and has a water vapor transmission rate value of at least about 1000 g/sq.m/24 hr., suitably at least about 2000 g/sq.m/24 hr, desirably about 3000 g/sq.m/24 hr. An example of a suitable material for backsheet 20 is a microporous polymer film, such as those commercially available from Mitsubishi through Marubeni Specialty Chemicals, Inc., White Plains, N.Y., under the trade designation C process (B Type) or LE process (D type), or available from The 3M Company, St. Paul, Minn., under the trade designation XK0-8044.

Backsheet 21 is suitably composed of a substantially liquid-impermeable material which is also substantially impermeable to vapor. In particular, the backsheet is substantially impermeable to at least water and water vapor. An example of a suitable backsheet material is a polymer film composed of polyethylene, polypropylene, or the like. Typically, the polymer film has a thickness within the range of about 0.0007–0.002 inch (0.0018–0.0051 cm). Backsheet 21 may alternatively be composed of a nonwoven fibrous web constructed to provide the required level of liquid Impermeability. For example, a nonwoven web composed of spunbonded or meltblown polymer fibers may be selectively treated with a water repellent coating or laminated with a liquid-impermeable polymer film. In a particular embodiment of the invention, backsheet 21 may comprise a nonwoven web composed of a plurality of randomly deposited hydrophobic thermoplastic meltblown fibers which are sufficientially bonded or otherwise connected to one another to provide a substantially vapor-impermeable and substantially liquid-impermeable web. The backsheet may also comprise a vapor-permeable nonwoven layer which has been partially coated or otherwise configured to provide liquid impermeability in selected areas.

For the purposes of the present invention, a substantially liquid-impermeable material is constructed to allow the passage of not more than about 0.05 ml of water within 5 seconds after applying a static pressure head of 70 cm of water to the material. Also, for the purposes of the present invention, a substantially vapor-impermeable material is constructed to provide a water vapor transmission rate (WVTR) of not more than about 30 g/sq./24 hr. A suitable technique for determining the WVTR value is the WVTR Test which is described in further detail herein below.

Topsheet layer 22 is typically composed of a liquid-permeable, substantially hydrophobic fibrous material, such as a spunbonded web composed of synthetic polymer filaments. Alternatively, topsheet 22 may comprise a meltblown web or a bonded-carded-web composed of synthetic polymer filaments. Suitable synthetic polymers include, for example, polyethylene, polypropylene and polyesters. In a particular aspect of the invention, the polymer filaments have a denier within the range of about 1.5–7 d and, preferably, have a denier within the range of about 1.5–3 d to provide improved performance. The filaments are arranged to form a layer having a basis weight within the range of about 20–34 grams per square meter (gsm) and, preferably, are arranged to have a basis weight of about 27 gsm. In addition, the topsheet layer has a bulk thickness within the range of about 0.008–0.017 inch (about 0.0203–0.0432 cm) and, preferably, has a bulk thickness within the range of about 0.010–0.12 inch (about 0.0254–0.305 cm) for improved effectiveness. The bulk thickness is measured under a restraining pressure of 0.014 psi (0.096 kPa).

Topsheet 22 may optionally be treated with surfactants to adjust its degree of hydrophobicity and wettability. It can also be selectively embossed or apertured with discrete slits or holes extending therethrough.

Absorbent body 24 typically includes a pad composed of airlaid, cellulosic fibers commonly referred to as wood pulp fluff. Other natural fibers, such as cotton, may also be employed to form the pad. Conventional absorbent pads can have a density ranging from about 0.03–0.40 grams per cubic centimeter, suitably from about 0.05–0.20 grams per cubic centimeter, and are sufficiently flexible to readily conform to the body of the wearer. Absorbent body 24 may also include a coform material composed of a mixture of cellulosic fibers and synthetic polymer fibers. For example, the coform material may be composed of an airlaid blend of cellulosic fibers and meltblown polyolefin fibers, such as polyethylene and/or polypropylene fibers. Particular examples of the coform material include 2–15 weight percent of polyethylene and/or polypropylene fibers. In one aspect of the invention, the fibrous material comprising absorbent body 24 is composed of filaments having a coarseness of about 10–20 mg/100 meters and, preferably, having a coarseness within the range of about 10–18 mg/100 meters. The filaments are arranged to form a layer having a basis weight within the range of about 400–1200 gsm and, preferably, having a basis weight of about 800 gsm. In addition, the absorbent body material typically has a bulk thickness within the range of about 0.17–0.21 inch (about 0.432–0.533 cm) as measured under a restraining pressure of 0.068 psi (0.47 kPa).

Absorbent body 24 may also include an effective amount of an inorganic or organic high absorbency (e.g. superabsorbent) material to enhance the absorptive capacity of the absorbent body. For example, absorbent body 24 can contain 5–99 weight percent high absorbency material and, preferably, includes about 20–60 weight percent of the high absorbency material to provide more efficient performance. Suitable inorganic high absorbency materials include, for example, absorbent clays and silica gels. Organic high absorbency materials can include natural materials, such as agar, pectin, guar gum and peat moss, as well as synthetic materials, such as synthetic hydrogel polymers. Such hydrogel polymers include, for example, carboxymethylcellulose, alkali metal salts of polyacrylic acids, polyacrylamides, polyvinyl ethers, hydroxypropyl cellulose, polyvinyl morpholinone, polymers and copolymers of vinyl sulfonic acid, polyacrylates, polyacrylamides, polyvinyl pyridine, and the like. Other suitable polymers include hydrolyzed acrylonitrile grafted starch, acrylic acid grafted starch, and isobutylene maleic anhydride copolymers, and mixtures thereof. The hydrogel polymers are preferably lightly cross-linked to impart desired levels of water insolubility to the material. Crosslinking may, for example, be by irradiation or by covalent, ionic, Van der Waals, or hydrogen bonding. Suitable materials are available from various commercial vendors, such as Dow Chemical Company, Hoechst Celanese Corporation, Allied-Colloid, and Stockhausen. Typically, the high absorbency material is capable of absorbing at least about 15 times its weight in water and, preferably, is capable of absorbing at least about 25–50 times its weight in water.

The high absorbency material can be distributed or otherwise incorporated into absorbent body 24 by employing various techniques. For example, the high absorbency material can be incorporated into a separate carrier sheet which is layered with a body of airlaid cellulosic fibers. Alternatively, the high absorbency material may be substantially uniformly distributed within the mass of fibers comprising the absorbent body. The material can also be non-uniformly distributed among the fibers to form, for example, a generally continuous gradient with either an increasing or decreasing concentration of high absorbency material as determined by observing the concentration moving from the bodyside of absorbent body 24 toward the outerside of the absorbent body. The high absorbency material may also comprise one or more discrete layers, strips, or pockets selectively segregated from the fibrous material of absorbent body 24.

The high absorbency material can itself be configured in various particle shapes. For example, particles of high absorbency material may be configured in the form of granules, flakes, fibers, or the like.

Optionally, a substantially hydrophilic tissue wrapsheet (not illustrated) may be employed to help maintain the integrity of the airlaid fibrous structure of absorbent body 24. The tissue wrap sheet is typically placed about the absorbent body over at least the two major facing surfaces thereof and composed of an absorbent cellulosic material, such as creped wadding or a high wet-strength tissue. In one aspect of the invention, the tissue wrap can be configured to provide a wicking layer which helps to rapidly distribute liquid over the mass of absorbent fibers comprising the absorbent body. In another aspect of the invention, the wrapsheet material on one side of the absorbent fibrous mass may be bonded to the wrapsheet located on the opposite side of the fibrous mass. The bonds are positioned at discrete, separate regions and extend through the thickness of the fibrous mass. Such a configuration effectively shapes the wrapsheet to form a plurality of individual "funnels" or "quilts" which can help to direct liquids into the interior of the fibrous mass and provide a more rapid absorption of the liquid. An effective embodiment may further include a plurality of holes or apertures formed at least partially through the thickness of the fibrous mass. The embodiment is configured such that the bonding of the oppositely positioned layers of wrapsheet material occurs through these holes or apertures. The apertures limit the amount of intervening fibrous material and allow a more direct bonding between the wrapsheet layers. The bonding can comprise adhesive bonds, sonic bonds, thermal-bonds, or the like.

Humidity transfer material 32 is located between the topsheet 22 and the absorbent body 24. The humidity transfer material serves to facilitate the movement of air within the diaper. Specifically, it is hypothesized that the humidity transfer material serves as a conduit through which water vapor can move from the intermediate section of the interior of the diaper (when in use) to the front and/or rear waistband section of the diaper in which the humidity transfer area is located. Once in the humidity transfer area, water vapor can be transferred out of the interior of the diaper through the vapor-permeable backsheet layer 20 or the vapor-permeable panel 56.

The humidity transfer material may suitably be formed from a nonwoven, (e.g., spunbond, meltblown or carded), woven, or knitted fibrous webs composed of natural fibers and/or synthetic polymeric fibers. Suitable fibers include, for example, acrylic fibers, polyolefin fibers, polyester fibers, or blends thereof. The humidity transfer material may also be formed from a porous foam material such as an open-celled polyolefin foam, a reticulated polyurethane foam, and the like. The humidity transfer material suitably has a wet compression recovery of at least about 74 percent, preferably at least about 87 percent, as determined as set forth below. In order to possess the desired degree of wet compression recovery, the humidity transfer material is suitably formed from materials which are hydrophobic. The hydrophobic materials may be treated with a material such as a surfactant to adjust the wettability thereof. Nonetheless, the humidity transfer material will generally remain less hydrophilic than the material which forms the absorbent body 24.

Thickness is an important parameter for humidity transfer material 32 and can be measured under both a low constraining pressure (0.207 kPa) and a high constraining pressure (50.37 kPa). A suitable device for performing the high pressure (50.37 kPa) thickness measurement is a Testing Machine, Inc., Model 49-70 Bulk Testing Apparatus with a 1.59 cm diameter platen. The low pressure, 0.03 psi (0.207 kPa), thickness measurement can be performed with a thickness measuring apparatus which employs a circular, 7.62 cm (3 inch diameter) platen to exert a pressure of 0.03 psi onto a sample placed on a non-resilient, rigid surface. For example, a suitable instrument for measuring bulk thickness at the low pressure includes a Starrett™ granite surface plate which is available from L. F. Starrett Company, located in Aphol, Mass. The instrument further includes a movable 7.62 cm diameter platen actuated by a Clipper air valve foot petal assembly, Catalog #3C30A2-S, which is available from Linemaster Switch Corporation, located in Woodstock, Conn. The thickness readout is provided by a Digimatic Indicator manufactured by Mitutoyo Manufacturing Company Limited, Japan, and distributed by MTI Corporation of Paramus, N.J. The indicator has a range between 0.001–2.0 inches.

To provide a desired degree of effectiveness, humidity transfer material 32 suitably has a dry bulk thickness dimension (at 0.207 kPa) of at least about 0.1 centimeter and, preferably, has a dry bulk thickness within the range of about 0.2–1.5 centimeter. When measured at 50.37 kPa, humidity transfer material 32 suitably has a dry bulk thickness of at least about 0.1 centimeter and, preferably, has a dry bulk thickness within the range of about 0.2–1.5 centimeter. If humidity transfer material 32 is too thin, it may not provide a sufficient amount of separation and spacing between topsheet 22 and absorbent body 24. Similarly, if the combined bulk thickness of topsheet 22 and humidity transfer material 32 is too thin, there may be insufficient separation and spacing between absorbent body 24 and the skin of the wearer. Accordingly, humidity transfer material 32 and topsheet 22 have a combined bulk thickness (at 0.207 kPa) of at least about 0.13 centimeter and, preferably, have a combined bulk thickness within the range of about 0.3–1.6 centimeter. When measured at 50.37 kPa, the combined bulk thickness of topsheet 22 and humidity transfer material 32 is at least about 0.13 centimeter and, preferably, is within the range of about 0.3–1.6 centimeter.

The humidity transfer material can have a basis weight of at least about 50 grams per square meter (gsm). In particular aspects of the invention, the basis weight is at least about 80 gsm and, preferably, is at least about 120 gsm to provide improved effectiveness. In other aspects of the invention, the basis weight is not more than about 320 gsm and, preferably, is within the range of about 120–160 gsm.

In a particular aspect of the invention, the humidity transfer material is configured to maintain a desired level of dryness. In particular, the humidity transfer material can be constructed to advantageously yield a desorption ratio of at least about 100. The desorption ratio can be determined as follows:

A humidity transfer material sample measuring 2 inches×2 inches in size is weighed and then immersed in a saline solution such as S/P certified blood bank saline solution for 1 minute. The saline is made by Stephens Scientific of Riverdale, N.J., and distributed by Baxter Healthcare of McGraw Park, Ill., under catalog ≐B3158-1. The sample is removed from the saline solution, placed on a clip for suspension in a vertical position from a ring stand, and allowed to drip for 1 minute. After this 1-minute drip period, the sample and any retained liquid are weighed. The sample is then placed on a desorption pad for 1 hour under a pressure of 3.45 kPa which is applied over substantially the entire surface of the sample. The sample, and any liquid remaining therein, are weighed after the one-hour desorption period. The desorption pad measures 2 inches by 2 inches and is composed of an airlaid mixture of wood pulp fluff and superabsorbent material in a ratio of about 1:1 based on weight. The wood pulp fluff is a softwood bleached pulp available from Kimberly-Clark Corporation (trade designation CR-54). The superabsorbent material is a sodium salt of a polyacrylic acid available from Hoechst Celanese Corporation under the trade designation IN 5000. The desorption pad has a basis weight of about 650 grams per square meter.

The desorption ratio is calculated as follows:
Desorption ratio=A/B
Where:
    A=weight gain of sample after the saturation/drip process
    B=weight gain of sample after the 1-hour desorption process When the humidity transfer material is fibrous, the fibers are configured to have a denier within the range of about 1–32 d and, preferably, have a denier within the range of about 3–10 d. When the humidity transfer material is a porous foam, the foam is suitably open celled and defines an average cell size of at least about 0.5 millimeter, suitably from about 1.0 to about 5.0 millimeters. The average cell size is suitably determined by methods known to those skilled in the art, such as image analysis or scanning electron microscopy.

To maintain the desired effectiveness of humidity transfer material 32, the material should be capable of sustaining its above-described isolation function even when wetted by urine or other aqueous liquids discharged from the wearer. Accordingly, the wet compression recovery value of humidity transfer layer 32 is at least about 74 percent.

Preferably, the wet compression recovery value is at least about 87 percent and, more preferably, is at least about 97 percent to provide improved performance.

The compression recovery value is a measure of the "springiness" or resilience of the material and can be determined by the procedure set forth below in the Test Procedures section.

In a further aspect of the invention, the humidity transfer material includes a plurality of two or more individual layers positioned in facing adjacent relationship. For example, 2–5 individual layers may be located between the topsheet and the absorbent body and together collectively comprise the humidity transfer material 32.

The individual layers forming the humidity transfer material may be distinct and separate from each other but may be Joined at selected, limited locations to maintain the integrity of the assembly. For example, the individual layers may be spot bonded to each other at limited, discrete locations.

The humidity transfer area 30 is generally that area of the diaper in which water vapor can transfer from the inside of a diaper, when in position on a wearer, to the outside of the diaper. That is, it is the area over which humidity can transfer from the humidity transfer material 32, through any intervening layer of material, and out the vapor-permeable backsheet 20 or the vapor-permeable panel 56. The area 30 illustrated in FIG. 1 includes the entire area in which the humidity transfer material 32 is in direct face-to-face overlapping relationship with the vapor-permeable backsheet 20. While in the embodiment illustrated in FIG. 1, the entire backsheet 20 is vapor permeable, Applicants have discovered that, when wetted, the absorbent body 24 forms a relatively effective barrier to the transfer of water vapor from the interior area defined by the diaper when in use, through the absorbent body, and through the backsheet layer 20.

Specifically, Applicants have discovered that, when the absorbent body 24 comprises a relatively high concentration of high absorbency material (greater than about 30 weight percent, preferably greater than about 40 weight percent) and has a relatively high density (greater than about 0.15 grams per cubic centimeter, preferably greater than about 0.20 grams per cubic centimeter), the absorbent body effectively blocks the transfer of water vapor from the interior of the diaper, when in use, through the vapor-permeable backsheet in those areas of the diaper where the absorbent cover overlays the backsheet, such as in the intermediate section 16 of the diaper 10. In many instances this is desirable since a high degree of transfer of humidity across the entire surface of the diaper has been found to produce a clammy feeling on the outer surface of the diaper which many consumers perceive in a negative manner.

Thus, in one embodiment of the present invention, the absorbent body is constructed to have a water vapor transmission rate value, when wet, which is less than the water vapor transmission rate value of the vapor-permeable backsheet 20. It is generally desired that the humidity transfer material has a water vapor transmission rate value, when wet, which is equal to or greater than said backsheet 20. When the humidity transfer material has a water vapor transmission rate value, when wet, which is equal to or greater than said vapor-permeable backsheet, and the absorbent body has a water vapor transmission rate, when wet, which is less than the water vapor transmission rate value of said vapor-permeable backsheet, the humidity transfer from the Interior of the diaper to the ambient atmosphere (exterior of the diaper) occurs generally in the humidity transfer area 30.

Humidity transfer area 30 generally has an area of at least about 5.0 square centimeters, alternatively of at least about 22 square centimeters, and preferably from about 45 to about 90 square centimeters.

The humidity transfer material may extend completely or partially over the humidity transfer area. It is generally desired that the entire humidity transfer area be overlaid with the humidity transfer material. This allows for the maximum degree of humidity transfer. As used herein, reference to humidity transfer refers to the transfer of water vapor from the interior of a diaper, when in use on a wearer, to the exterior of the diaper (ambient atmosphere). Further, the humidity transfer material may extend completely or partially over the adjacent surface of the absorbent body 24. The humidity transfer material is suitably located over the intermediate section 16 of the diaper and is substantially centered side-to-side with respect to the longitudinal centerline 58 of the diaper. The humidity transfer material suitably extends over about 35 to about 100 percent of the total length 26 of the backsheet layer. The humidity transfer material may extend over about 50 to about 100 percent of the width of the diaper as measured at the narrowest portion of the diaper intermediate section 16. It is generally preferred that the humidity transfer material extend at least from the Intermediate section to the waistband section which includes the humidity transfer area.

In the embodiment illustrated in FIG. 2, the humidity transfer area is formed in the vapor-Impermeable backsheet layer 21 by the vapor-permeable panel 56. The vapor-permeable panel 56 is substantially liquid impermeable, but is vapor permeable. In this embodiment, the vapor-permeable panel 56 is located wherever it Is desired to provide a humidity transfer area 30. The vapor-permeable panel 56 suitably has a water vapor transmission rate value of at least about 2500 g/sq.m/24 hr, suitably at least about 3000 g/sq.m/24 hr, and alternatively at least about 4200 g/sq.m/24 hr, to provide improved performance. Further, the vapor-permeable panel 56 has an effective breathable area of at least about 5.0 square centimeters, suitably at least about 22.0 square centimeters, and preferably within the range from about 45 to about 90 square centimeters.

If vapor-permeable panel 56 Is partially covered or occluded by another, substantially vapor-impermeable component of diaper 10 or 11, the areal extent of vapor-permeable panel 56 should be appropriately increased to compensate for the breathable area obscured by the occluding component. For example, when adhesive tapes are used as fastening means for the diaper, a tape landing zone composed of a plastic film may be attached to the outward surface of vapor-permeable panel 56 to provide a refastenable adhesive tape system. While the plastic film may be vapor permeable or vapor impermeable, the securement of such a tape landing zone over the vapor-permeable panel could excessively occlude a portion of the vapor-permeable panel and might require an increase of the breathable surface area at other locations of panel 56. Similarly, where the diaper includes a hook-and-loop fastening system, such as a Velcro™-type fastener, the loop material may be located over an outwardly-facing surface of vapor-permeable panel 56. While the loop material may itself be vapor permeable, the adhesive or other bonding system employed to secure the loop material over vapor-permeable panel 56 may be substantially vapor impermeable. To reduce the amount of occlusion of panel 56, a discontinuous, open pattern of the adhesive or other bonding mechanism may be employed to secure the loop material onto the vapor-permeable panel. For example, where in adhesive is employed, an open pattern of sprayed droplets or sprayed filaments may be employed to secure the component onto the panel.

Vapor-permeable panel 56 may be composed of a microporous polymer film, such as Grade PMP-1 film, manufactured by Mitsui Toatsu Chemical, Inc., Tokyo, Japan. Alternatively, vapor-permeable panel 56 may be composed of a nonwoven fibrous material, such as a spunbonded or meltblown web composed of synthetic polymer fibers. Vapor-permeable panel 56 is preferably non-elastic.

In a particular aspect of the invention, vapor-permeable panel 56 is composed of a calendared, composite, fibrous web which includes a barrier layer comprising fine fibers and a reinforcing layer comprising coarse fibers. The barrier layer and reinforcing layer are securely bonded together by fusing or adhering the reinforcing fibers into the barrier fibers, and the reinforcing layer is configured to form the outwardly facing surface of the composite web.

The reinforcing layer of the composite can be a web of hydrophobic fiber material arranged to provide a web basis weight within the range of about 10–35 grams per square meter. The reinforcing layer has a grab tensile strength (ASTH test method 149 W) within the range of about 1500–10,000 grams/inch and is bonded with a spot bonding pattern which covers between about 3–20 percent of the surface area of the reinforcing layer. The barrier layer of the composite is a web of hydrophobic fiber material arranged to provide a basis weight within the range of about 10–60 gsm. The barrier layer is composed of a plurality of randomly deposited, essentially continuous, hydrophobic, thermoplastic fibers which are partially bonded to one another. Such a web may be produced by meltblowing a web composed of thermoplastic polymer micro-fibers having an average cross-sectional diameter of about 3.0 micrometers or less.

The barrier layer and reinforcing layer are securely bonded to each other with a discontinuous bond pattern composed of thermal bonds, sonic bonds, thermal or pressure activated adhesive resin, or the like. This interlayer bonding pattern covers an area within the range of about 3–20 percent of the surface area of the composite web. A suitable composite web exhibits a Frazier porosity value within the range of about 3–15.25 cubic meters/minute/square meter and can support a hydrohead of at least 70 cm of water for a period of 5 seconds with a visible leakage therethrough of no more than a drop (0.05 cc) of water.

As representatively shown in FIG. 2, vapor-permeable panel 56 is a separate component which connects to and extends laterally and longitudinally across the front waistband section 12 of the diaper 11. Vapor-permeable panel 56 may extend across the complete cross-directional width of diaper 11. Alternatively, vapor-permeable panel 56 may extend partially across the diaper cross-directional width. For example, the vapor-permeable panel may comprise a sheet component which spans across a notch, or recess, or a "window"-type opening formed into the layer of backsheet material 21. To provide the desired amount of breathable surface area, panel 56 can have a longitudinal dimension within the range of about 2–18 centimeters and a width dimension within the range of about 2–21 centimeters. The shown embodiment of panel 56 begins at the terminal, front waistband edge of the absorbent body 24. While the illustrated embodiment shows a panel 56 which does not extend completely to the terminal, waistband edge of the diaper article, it should be readily appreciated that the extent of panel 56 along the diaper longitudinal direction may optionally extend to the terminal, waistband edge.

In a particular aspect of the invention, the humidity transfer material has a Moisture Retention Index of not more than about 40 grams. Preferably, the humidity transfer material has a Moisture Retention Index of not more than about 30 grams and, more preferably, has a Moisture Retention Index of not more than about 25 grams. The low Moisture Retention Index of the humidity transfer material can advantageously help limit the occluding effect produced by the presence of held liquids. As a result, water vapor can more readily escape from the spaces adjacent the wearer's skin.

The humidity transfer material can also be advantageously configured to have a Wicking Index of not more than about 0.5 gram. Preferably, the humidity transfer material has a Wicking Index of not more than about 0.2 gram and, more preferably, has a Wicking Index of not more than about 0.02 gram to provide Improved effectiveness. The relatively low Wicking Index of the humidity transfer material helps to limit the presence of liquid which could inhibit the movement of water vapor away from the wearer's skin.

Other diaper configurations suitable for use in connection with the instant application, other diaper components suitable for use on diapers, and other articles of the present invention are described, for example, in U.S. Pat. No. 4,798,603 Issued Jan. 17, 1989, to Meyer et al.; U.S. Pat. No. 5,176,668 issued Jan. 5, 1993, to Bernardin; U.S. Pat. No. 5,176,672 issued Jan. 5, 1993, to Bruemmer et al.; U.S. Pat. No. 5,192,606 issued Mar. 9, 1993, to Proxmire et al., and U.S. Pat. application Ser. No. 08/096,654 filed Jul. 22, 1993, in the name of Hanson et al, issued Apr. 23, 1996, as U.S. Pat. No. 5,509,915.

Other suitable diaper components which may be incorporated on absorbent articles of the present invention include containment flaps, waist flaps, tape fasteners, hook-and-loop fasteners, elastomeric side panels, and the like.

In those instances where there is an undesirable level of liquid passing out of the diaper in the humidity transfer area, it may be desirable to employ an absorbent insert. The absorbent insert may be formed from the same types of material used to form absorbent body 24 and may have the same properties and characteristics as absorbent body 24. The absorbent insert suitably overlies a portion of the humidity transfer area, specifically the vapor-permeable panel 56. The absorbent Insert is located between the humidity transfer material on a body of a wearer when in use. In this position, the absorbent insert can function to desorb and hold fluid from the humidity transfer material and prevent the liquid in the humidity transfer material from passing out of the diaper in the humidity transfer area. The absorbent insert is typically located between the humidity transfer material and the topsheet layer.

In another aspect of the invention, the diaper can advantageously be constructed to provide for a mean net skin hydration value (mean net SHV) of not more than about 5 $g/m^2$ in 30 minutes. Preferably, the diaper is constructed to provide a mean net SHV of not more than about 3 $g/m^2$ in 30 minutes for improved effectiveness. Such mean net SHV's are indicative of lower levels of skin wetness as compared to the excessive levels of skin wetness which can occur in conventional diapers after they have been wetted. The lower levels of skin wetness can help make the skin less susceptible to abrasion and less susceptible to chemical or biological Irritants.

TEST PROCEDURES

Water Vapor Transmission Rate

A suitable technique for determining the WVTR (water vapor transmission rate) value of a material is as follows. For the purposes of the present invention, 3-inch diameter (76 millimeter) circular samples are cut from the test material and from a control material, Celguard™ 2500 (Hoechst Celanese Corporation). Two or three samples are prepared for each material. Test cups used for testing are cast aluminum, flanged, 2 inches deep and come with a mechanical seal and neoprene gasket. The cups are distributed by Thwing-Albert Instrument Company, Philadelphia, Pa., under the designation Vapometer cup #681. One hundred milliliters of distilled water are poured into each Vapometer cup, and each of the individual samples of the test materials and control material are placed across the open top area of an individual cup. Screw-on flanges are tightened to form a seal along the edges of the cups leaving the associated test material or control material exposed to the ambient atmosphere over a 62 millimeter diameter circular area (an open, exposed area of about 30 $cm^2$). The cups are then weighed, placed on a tray, and set in a forced air oven set at 100° F. (37° C.). The oven is a constant temperature oven with external air circulating through it to prevent water vapor accumulation inside. A suitable forced air oven is, for example, a Blue N Power-O-Matic 60 oven distributed by Blue N Electric Co. of Blue Island, Ill. After 24 hours, the cups are removed from the oven and weighed. The preliminary, test WVTR value is calculated as follows:

$$\text{Test WVTR } (g/m^2/24 \text{ hours}) = \frac{[(\text{grams weight loss over 24 hours}) \times 7571]}{24}$$

The relative humidity within the oven is not specifically controlled.

Under predetermined set conditions of 100° F. and ambient relative humidity, the WVTR for Celguard 2500 has been determined to be 5000 $g/m^2/24$ hours. Accordingly, Celguard 2500 is run as a control sample with each test.

Celguard 2500 is a 0.0025 cm thick film composed of a microporous polypropylene.

Frazier Porosity

The Frazier Porosity values referred to in the present specification can be determined employing a Frazier Air Permeability Tester (Frazier Precision Instrument Co., Gaithersburg, Md.) and Method 5450, Federal Test Methods Standard No. 191A. For the purposes of the present invention, the test is conducted with a sample which measures 8 inches×8 inches.

Moisture Retention Index

Figure 3:
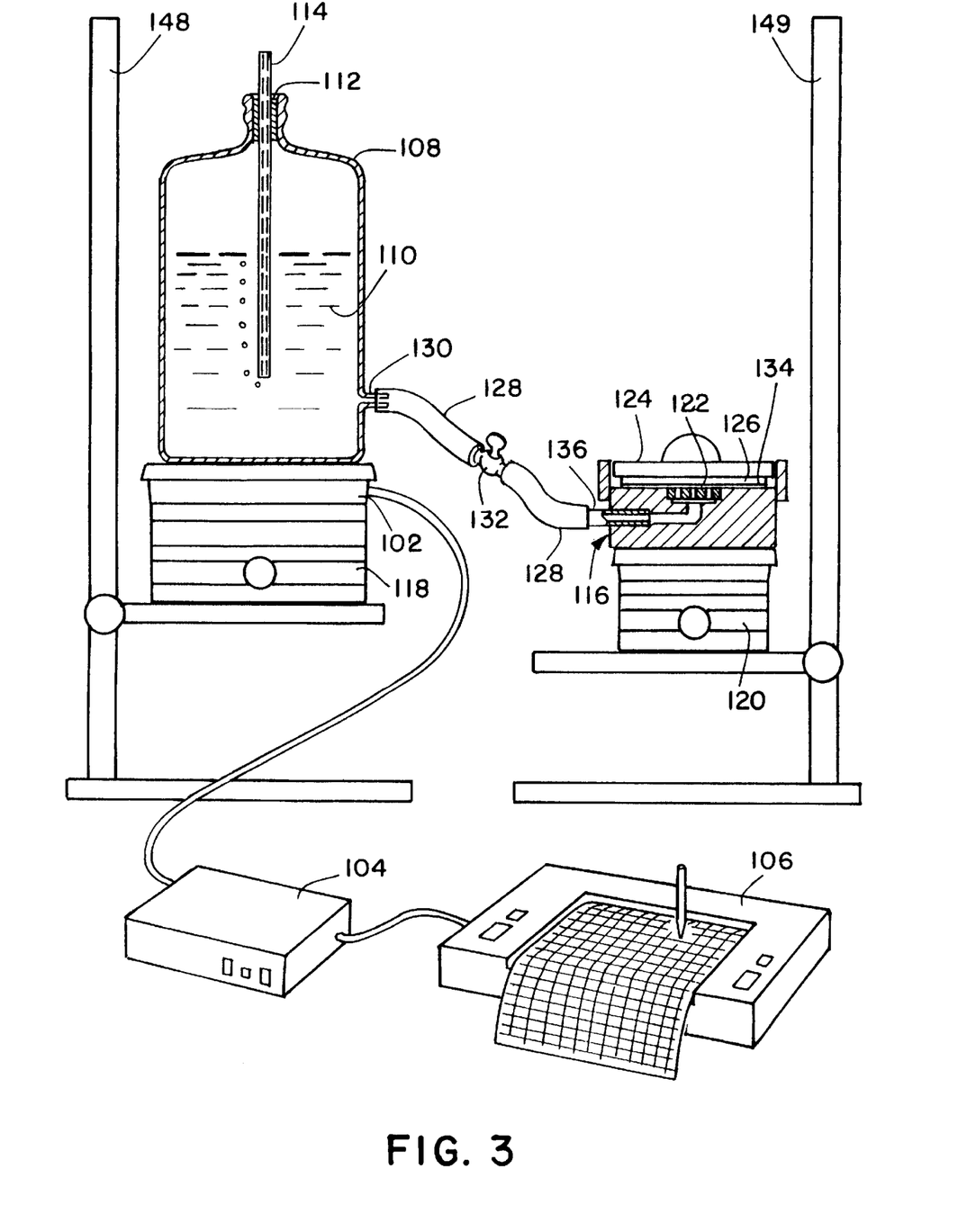
FIG. 3, 3A and 3B representatively show an apparatus for determining a Moisture Retention Index.

A suitable technique for determining the Moisture Retention Index of a section of humidity transfer material is as follows:

With reference to FIG. 3, a suitable testing apparatus for determining Moisture Retention Index includes an electronic balance 102 which is accurate to 0.01 gram and has at least a 1000 gram capacity. In addition, the balance has a digital signal output for use with a digital-to-analog converter 104 and a chart recorder 106. A second electronic balance is employed to weigh the test samples. A suitable electronic balance, for example, is a Mettler PC2200 manufactured by Mettler Instrument Company, a business having offices located in Hightstown, N.J. The digital-to-analog converter should be compatible with electronic balance 102 and chart recorder 106. For example, in the illustrated embodiment, the digital-to-analog converter is a Mettler GC47 D/A Converter. A suitable chart recorder is, for example, a Fisher Recordall Series 5000 which is available from Houston Instrument, a company having offices located in Austin, Tx.

The apparatus further includes a 500 milliliter aspirator bottle 108 for holding a suitable reservoir supply of synthetic urine 110. A suitable synthetic urine could be saline, such as S/P certified blood bank saline made by Stephens Scientific of Riverdale, N.J., and distributed by Baxter Healthcare of McGraw Park, Ill. under catalog #3158-1. The aspirator bottle is configured with a size number 4 rubber stopper 112 and a 7-inch glass air tube 114 which has an inside diameter of 0.22 inches (5.58 m). Air tube 114 is positioned through a bore hole formed through the center of stop per 112 and is inserted until approximately 5 inches of the air tube protrudes from the inside surface of the stopper.

Figure 3A:
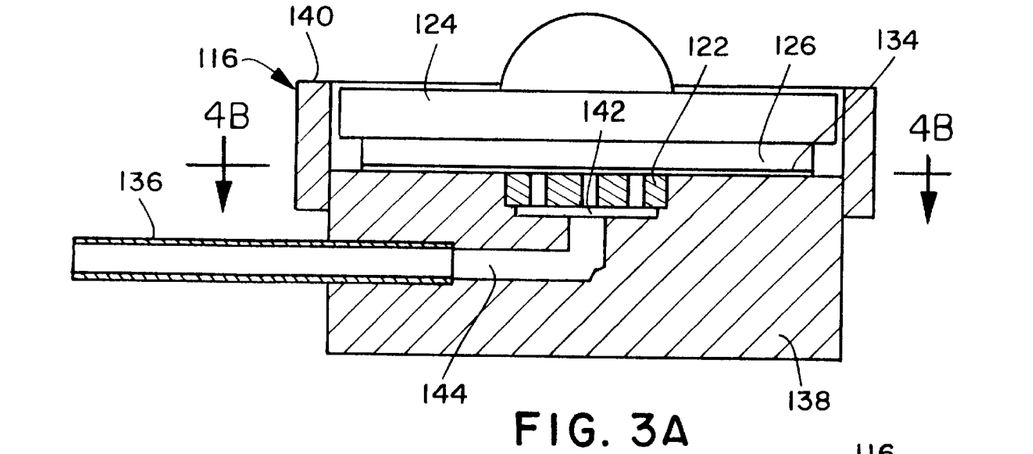
Figure 3B:
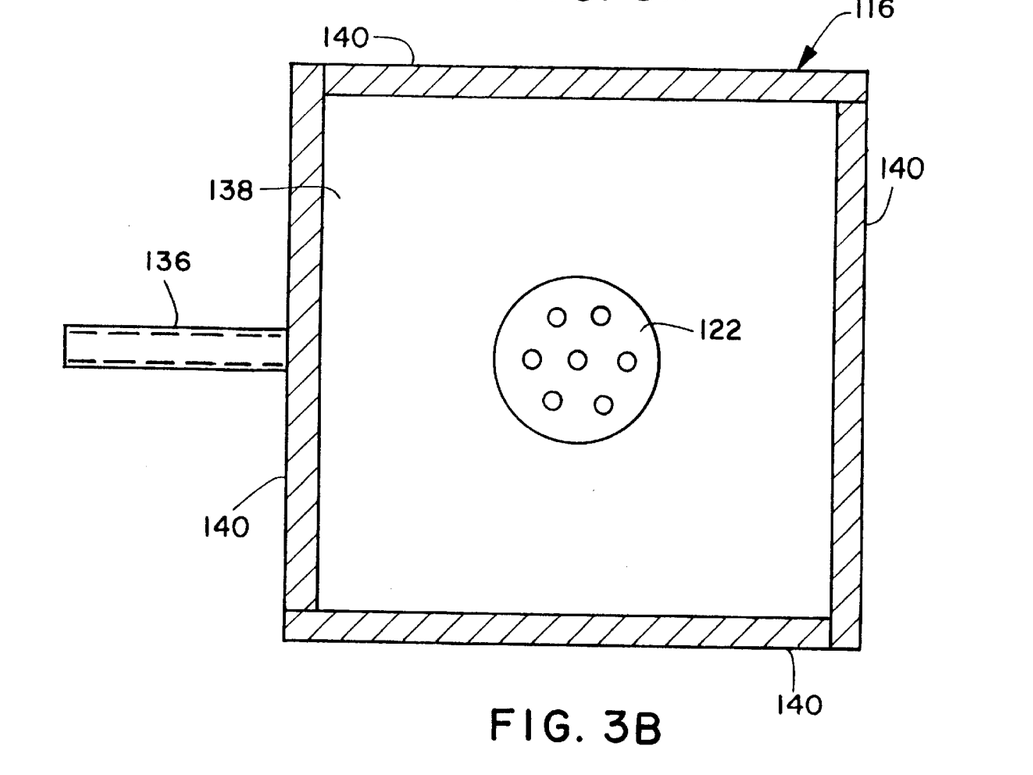

Enlarged side an d top views of absorbency test chamber 116 are representatively shown in FIGS. 3A and 3B. The test chamber is composed of a suitable material, such as lucite, and has a substantially square base area measuring 4 inches by 4 inches. The chamber includes a 4 inch×4 inch base member 138 and a ⅝ inch (about 1.59 cm) high wall member 134 situated along each of the four sides 140 of the base member. A 125 gram cover 124 is configured for placement over the sample placed within chamber 116. The cover extends over a generally square area and is configured to be slightly smaller than the top opening into chamber 116. Accordingly, the cover can sufficiently prevent the evaporation of moisture and can readily slip along the walls of the chamber to provide a selected pressure onto the top of a sample placed therein. A stepped, circular recess 142 is formed into the top of base 138, and conduit 144 extends through the base to a 0.25 inch inside diameter outlet tube 136. Conduit 144 conducts liquid into the bottom of recess 142 where it is then transmitted through a multiport transfer plate to a test sample 126. Within the test chamber, a 1.25 inch diameter multipart plate 122 composed of lucite sits in recess 142 resting on top of the step therein. The multiport plate includes seven ports, each being 3 mm in diameter, with one port located in the center of plate 122 and the remaining six ports arranged radially from the center port and equally spaced circumferentially around the center port along a 1 3/16 inch (about 3.016 cm) diameter circle. The seven ports are positioned 3/8 inch apart center-to-center, and plate 122 is centrally located within chamber 116. Plastic tubing having a 0.25 inch inside diameter, such as Tygon tubing-R3603, interconnects outlet tube 130 of reservoir bottle 108 and tube 136 which enters base 138. Plastic tubing 128 has an approximate total length of 7.5 feet, but the exact lengths are not critical. The tubing lengths should allow for easy use of the apparatus but should not be excessive. A control valve, such as a two-way polypropylene stopcock 132, regulates the liquid flow through plastic tubing 128. Stopcock 132 has a bore size of 4 millimeters so as not to excessively restrict liquid flow. Laboratory jacks are employed to regulate the vertical positioning of the components of the testing apparatus. In particular, laboratory jack 118 supports electronic balance 102 and reservoir bottle 108, while laboratory jack 120 supports test chamber 116 and the components contained therein. Laboratory stands 148 and 149 can be employed to make any large, coarse adjustments of the vertical positions of the components of the testing apparatus.

The testing apparatus should be clean and free from bacterial contamination and salts which may have settled out of the synthetic urine. During testing, the test equipment should not be handled. If the tubing is removed or handled, an equilibration time of approximately one hour should be employed to allow relief of any stresses imparted to the tubing. This equilibration time should also be allowed when refilling reservoir bottle 108. The tubing should not be touched during testing. The humidity transfer material being tested should be preconditioned at "standard" conditions of 50±2 percent RH and 23±1 degrees Centigrade. The appointed bodyside of the absorbent material should be positioned facing multiport plate 122. Any detergents employed to clean any components of the apparatus should be completely removed so as not to affect the surface tension of the synthetic urine employed to conduct the tests.

Prior to testing, reservoir bottle 108 is filled with synthetic urine and a portion of the liquid is drained through the tubing to completely remove all air bubbles from the tubing and from the fluid conduits in the testing apparatus. The drained synthetic urine is discarded and the stopcock is closed to stop the flow of liquid. The reservoir bottle is then refilled. Plastic tubing 128 should be free of sharp bends or kinks which might impede the flow of liquid and alter the test results.

Prior to testing, the equipment is also adjusted to establish a zero head. First, chamber 116 is leveled by placing a suitably sized bubble level indicator in the center of the chamber and by pushing slightly on the appropriate side of laboratory jack 120. The front and back of chamber 116 should also be leveled. At this point, testing chamber 116 may be taped in place on laboratory jack 120. Stopcock 132 is then opened to permit liquid flow, and a slightly concave meniscus is created in each of the seven 3 mm ports in plate 122 by adjusting the height of laboratory jack 120. Zero head is obtained when each of these ports contains synthetic urine with a slightly concave meniscus and an air bubble is maintained at the bottom of glass tube 114 within reservoir bottle 108. Stopcock 132 is then closed to stop the flow of liquid, and chamber 116 is checked to make sure that it is still level. The apparatus is then allowed to equilibrate for 3–6 hours. This equilibration time is not necessary when the testing apparatus is in continuous use and the liquid has not been changed or added. Chart recorder 106 is turned on and adjusted to plot at zero when the electronic balance 102 is at its zero setting.

The equilibrium setting of the testing apparatus is checked by placing cover 124 on chamber 116 and closing stopcock 132. Electronic balance 102 is then zeroed and the chart recorder is turned on. The testing apparatus is at equilibrium if the absorbed fluid weight reading is stable at zero. Preferably, the absorbed fluid weight reading should not vary by more than plus or minus 0.03 gram in 15 minutes.

Test sample 126 is configured in the shape of a 3-inch diameter disk. The sample is weighed to the nearest 0.01 gram and the weight is recorded. The thickness of the sample is measured with a 3-inch (7.62 cm) diameter platen under a restraining pressure of 0.2 psi (1.38 kPa).

A 3-inch diameter piece of filter paper, such as Whatman No. 4 filter paper, is centered over multiport plate 122 within chamber 116. Stopcock 132 is then opened to wet out the filter paper and remove all air bubbles. It should be noted that a new piece of filter paper is used for each test sample. The stopcock is then closed to stop the flow of liquid, and excess fluid is blotted from the edges of the filter paper. The center of the filter paper, however, is not blotted so as to avoid forming any air bubbles. The areas around filter paper 134 and cover 124 should both be dry. Stopcock 132 is opened and electronic balance 102 is zeroed out once it stabilizes.

The test is started by simultaneously placing and centering sample 126 over filter paper 134, with cover 124 resting on top of the sample, and turning on the chart recorder 106. Test sample 126 is then allowed to absorb fluid for a 30-minute testing period. At the end of this period, stopcock 132 is closed and chart recorder 106 is turned off. The final reading of the electronic balance is recorded on the chart paper to serve as a check of the chart recorder data. The Moisture Retention Index is the grams of synthetic urine absorbed by test sample 126 during the 30-minute test period.

Wicking Index

A suitable technique for determining the Wicking Index of a single, generally homogeneous material or of a composite material is as follows. With reference to the apparatus representatively shown in FIG. 4, the Wicking Test apparatus includes a chamber 150 having a 4 inch by 4 inch base measurement. A 3-inch diameter circular test sample 152 is weighed employing an electronic balance such as a Kettler PC2200 balance which is accurate to 0.01 gram. A 4-inch by 4-inch piece of 1.0 mil thick polyethylene film 160 is placed on the bottom of chamber 150, and a 3-inch diameter piece of retention material 154 is placed on top of the polymer film. The retention material is composed of an airlaid mixture of wood pulp fluff and superabsorbent in a ratio of about 1:1 based on weight. The wood pulp fluff is a softwood bleached pulp available from Kimberly-Clark Corporation (CR-54). The superabsorbent is a sodium salt of a polyacrylate available from Hoechst Celanese Corporation under the designation IN 5000. The resultant retention material 154 has a total thickness of 0.15 inch (measured under a load of 50.37 kPa) and a total basis weight of about 650 grams per square meter. The total dry weight of the retention material is about 3.5 grams, of which 50 weight percent is superabsorbent material.

Figure 4:
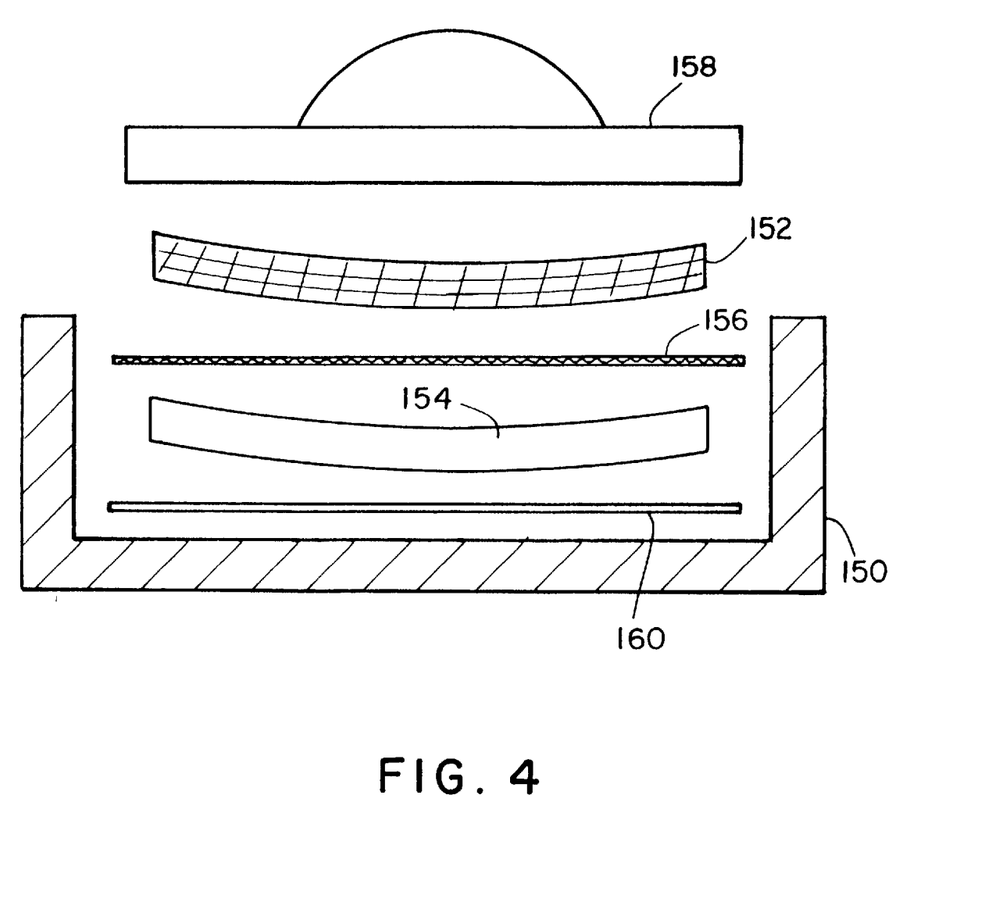
FIG. 4 representatively shows an apparatus for determining a Wicking Index.

After loading the retention material with 70 gm (ml) of synthetic urine (20 gram/gram liquid loading), a 4-inch by 4-inch piece of screen material 156 is placed on top of retention material 154. The screen material is a fiberglass mesh screen having the screen strands arranged in a generally square-grid pattern with 18 openings per lineal inch (324 openings per square inch) and a screen thickness of about 0.028 cm.

Test sample 152 is then placed on top of screen 156, and a 962 gram cover 158 is placed on top of the entire test sample 152 to impart a pressure of 0.3 psi. The cover extends over a generally square area and is configured to be slightly smaller than the top opening into chamber 150. Accordingly, the cover can sufficiently prevent the evaporation of moisture and can readily slip between the walls of the chamber to provide the selected pressure onto the top of a sample placed therein. Thirty minutes after placing weight 158 (cover) on top of test sample 152, the test sample is removed from chamber 150 and weighed to the nearest 0.01 gram. The difference between the dry sample weight and the "wet" sample weight after the 30-minute testing period is the amount of fluid "wicked" from the loaded retention material 154 into test sample 152. The amount of wicked liquid (in grams) is referred to as the Wicking Index.

Skin Hydration Value

Skin hydration values are determined by measuring total transepidermal water loss (TEWL) and can be determined by employing the following test procedure.

The test is conducted on partially toilet trained infants who have no lotions or ointments on the skin and have not been bathed within 2 hours prior to the test. Each infant tests one diaper during each test session. The test diapers Include a test code and a control code. The test diapers (test code and control code) are randomized.

Each test diaper is weighed before and after use to verify the volume of liquid added into the diaper. A felt tip pen is employed to mark an "X" at the target zone inside the diaper, with the "X" positioned 6.5 inches below the top front edge of the diaper and centered side-to-side. The TEWL measurements are taken with an evaporimeter, such as an Evaporimeter EP1 instrument distributed by Servomed AB, Stockholm, Sweden. Each test measurement is taken over a period of two minutes with TEWL values taken once per second (a total of 120 TEWL values). The digital output from the Evaporimeter EP1 instrument gives the rate of transepidermal water loss (TEWL) in $g/m^2/hr$. Skin hydration values (SHV) are in units of total amount of water loss per unit area measured during the two-minute sampling period and are calculated as follows.

$$SHV\,(g/m^2/hour) = \frac{\sum_{n=1}^{120} (TEWL)_n}{120}$$

A preliminary skin hydration value measurement is taken after a 15-minute "dryout" period when the infant wears only a long T-shirt or dress. The measurement is taken on the infant's lower abdomen, in a region corresponding to the target zone of the diaper, using the evaporimeter for the purpose of establishing the initial skin hydration value of the infant's skin at the diaper target zone. If the preliminary SHV is less than 10 $g/m^2$/hour, a diaper is then placed on the infant. If the preliminary SHV is greater than 10 $g/m^2$/hour, the "dryout" period is extended until a reading below 10 $g/m^2$/hour is obtained. Prior to securing the diaper on the infant, a tube is positioned to direct a flow of liquid to hit the premarked target zone. Once the diaper is secured, either 150 milliliters of adjusted 0.9 w/w percent aqueous saline (surface tension adjusted to 55 dynes/cm using Tween™ 20) is added in two insults of 75 milliliters each at a rate of 15 milliliters/second, or 225 milliliters of the adjusted 0.9 w/w percent aqueous saline is added in three insults of 75 milliliters each at a rate of 15 milliliters/second. The time between insults is 30 seconds.

The infant wears the diaper for 30 minutes after which a test measurement of skin hydration is taken on the lower abdomen corresponding to the target zone mark of the diaper. The measurement is taken over a 2-minute period. The used diaper is then weighed. Relative humidity and temperature measurements can be taken within the diaper prior to the skin hydration measurements being taken. The test procedure is then repeated the next day for each infant using the diaper type (test or control) which the infant has not yet worn.

The control diaper provided a standardized basis for comparing the performance of the diaper configuration being tested and evaluated. In the tests conducted for the purposes of the present invention, the control diaper was a handmade diaper which was identical in all relevant aspects to the commercially available HUGGIES™ Supreme diaper sold by Kimberly-Clark Corporation.

Data is discarded for any infants which have added to the loading of saline solution. The value reported for the mean net SHV (grams/$m^2$ in one hour) is the arithmetic mean for all infants of the post-wear skin hydration value, taken at the lower abdomen (target zone mark), minus the skin hydration value measured at the lower abdomen prior to placing the diaper on the infant (after "dryout" period). A separate mean net SHV is determined for the test code diapers and the control code diapers. The net skin hydration value is determined as follows:

Net $SHV_i$=Y−Z

Where:
Y=skin hydration value measured at target zone mark of an individual infant
Z=baseline skin hydration value measured on the lower abdomen after "dryout" period prior to placing diaper on the infant
$SHV_i$=skin hydration value for individual infant
Then, $$\text{Mean Net } SHV = \frac{\sum_{i=1}^{N} \text{Net } SHV_i}{N}$$

Where:
N=number of infants in study

The percent reduction in skin hydration is determined as follows:

$$\% \text{ Reduction} = \frac{\sum_{i=1}^{N} [((C - D)/C) \times 100]}{N}$$

Where:
C=Net $SHV_i$ for control diaper code
D=Net $SHV_i$ for test diaper code
N=number of infants in study Wet Compression Recovery Wet compression recovery is determined from void volume measurements and is measured using an INSTRON or SINTECH tensile tester which measures the resisting force as a material is compressed between a movable platen and a fixed base at a constant rate using a certain amount of force and subsequently releasing the force at the same rate. Preferably pressure, or force, and platen position are recorded. If only force is recorded, pressure is calculated using:

$$P = \frac{F}{A_P} \cdot 10,000 \text{ cm}^2/\text{m}^2$$

where:
P=pressure in Pascals
F=force pushing back on the platen in Newtons
$A_P$=area of the platen in square centimeters (18.9 cm$^2$)
Void volume for a given platen position is calculated using the equation:

$$VV = \frac{(x_o - x) \cdot A_m \cdot 0.1 \text{ cm/mm}}{M} - \frac{1}{p_{fiber}}$$

where:
VV=void volume of material in cubic centimeters per gram
$X_0$=initial platen position from the base in millimeters
x=platen position from initial position in millimeters
$A_m$=area of sample material in square centimeters
M=mass of sample material in grams
$P_{fiber}$=fiber density in grams per cubic centimeter
For webs made with multiple fiber types, the web fiber density is the weight average of each individual fiber density:

$$P_{fiber,\ Total} = \text{wt}\%_{fiber\ 1} \cdot P_{fiber\ 1} + \text{wt}\%_{fiber\ 3} \cdot P_{fiber\ 2} + \ldots$$

where:
wt %=weight percent of the fiber type in the web or $$\text{wt }\% = \frac{\text{fiber weight in composition}}{\text{total composition weight}} \times 100\%$$

When a foam material is being measured, $P_{fiber}$ is the density of the material from which the foam is fabricated. For foam materials, the void volume (VV) calculated using the preceding equation is an approximation, and the actual void volume will become less than the calculated void volume (VV) as the number of closed cells within the foam material increases.

The base must be larger in size than the platen. Zero height between platen and base distance was set by bringing the platen down until it barely touches the base. The platen was then raised to the desired initial height from the zero distance. The initial platen position must be greater than the initial thickness of the sample material so that the test starts out at zero pressure on the sample. The sample material can be the same size as the platen or larger.

Suitable equipment for this test could include:
Compression tester:
INSTRON model 6021 with compression test software and 1kN load cell made by Instron of Bucks, England
Balance:
Mettler of Highstown, N.J., model PM4600
For the purpose of measuring wet void volume for the present specification, a 4.9 cm diameter circular platen was used to compress materials against the base at a rate of 5.08 mm/min. up to a 1.92 kg load (10,000 Pascal or 1.45 lb/in$^2$ pressure). The platen was then returned at the same rate to the initial starting position. The initial starting position for the platen was the sample material thickness plus 1 mm from the base. Material samples were cut to 50.4 mm diameter circles and were tested in the center. Force and position data were recorded at uniform periods of time between 0.05 and 0.01 minute. The test is run on five material samples and the results averaged.

Wet void volume was measured when the material sample was completely immersed in 0.9% aqueous saline throughout the test. A flat bottomed container, such as a hexagonal polystyrene weighing dish catalog #02-202D from Fischer Scientific of Pittsburgh, Pa., was placed on the base, and the platen was zeroed and set to the initial position as described above. A 0.9% aqueous saline solution was added to the container to fill it to a level just to the bottom of the platen at its initial position. An appropriate saline could be S/P certified blood bank saline made by Stephens Scientific of Riverdale, N.J., and distributed by Baxter Healthcare of McGraw Park, Ill., under catalog #B3158-1. The load cell was tared with this level of fluid in the container. The sample was placed in the fluid, under the platen, and the test was then performed as described above. Buoyant force was found to have a negligible effect on pressure but, if so desired, it can be subtracted from the pressure readings at each platen position using the following equation:

$$P_B = p_{saline} \cdot g \cdot (x_o - x) \cdot \left| \frac{A_P}{A_d - A_P} + 1 \right| \cdot 0.01$$

where:
$P_B$=Pressure from buoyant force in Pascals
$P_{saline}$=saline (fluid) density in grams per cubic centimeter
$A_P$=area of the platen in square centimeters (18.9 cm$^2$)
$A_d$=area of the dish in square centimeters
$x_o$=initial platen position from the base in millimeters
x=platen position in millimeters
g=standard acceleration of gravity which is 981 cm/seconds$^2$
0.01=conversion factor=0.1 cm/mm·0.001 kg/gm·100 cm/m
The overall pressure on the sample becomes:

$$P_{sample} = P_{reading} - P_B$$

where:
$P_{sample}$=pressure on the sample from the platen in Pascal
$P_{reading}$=pressure reading from the SINTECH or INSTRON in Pascal
$P_B$=buoyancy pressure from the 0.9% saline in Pascal
For the purpose of measuring void volume for the present specifications, 120 ml of saline was placed in the container, and the platen was initially set a distance equal to 1 M greater than the thickness of the test material sample from the base.

Wet compression recovery was calculated using the platen positions on initial compression to 68.9 Pascal and on recovery when the pressure was equal to 68.9 Pascal:

$$\% \text{ Wet Compression Recovery} = \frac{VV_{recovery\ 68.9\ Pa}}{VV_{compress\ 68.9\ Pa}} \times 100$$

where:
$VV_{recovery\ 68.0\ Pa}$=void volume upon recovery at 68.9 Pascal pressure
$VV_{compress\ 68.9\ Pa}$=void volume upon initial compression to 68.9 Pascal pressure
The following examples are presented to provide a more detailed understanding of the invention. The specific materials and parameters are exemplary and are not intended to specifically limit the scope of the invention.

EXAMPLES

Example 1

The following humidity transfer materials are employed in this example.

Sample A

This humidity transfer material is a reticulated polyurethane foam commercially available from Illbruck, Incorporated under the trade designation Style #180,000 Federal Foam. The foam has a basis weight of 160 g/m$^2$, a bulk thickness of 0.6 cm (measured under a pressure of 0.207 kPa), and a bulk density of 0.027 g/cm$^3$. The material has a wet compression recovery of 97 percent, a moisture retention index of about 0.15 grams, and a wicking index of 0.02 grams.

Sample B

This humidity transfer material comprises a through-air bonded carded web formed from polyethylene/polyester sheath core fibers. The polyethylene material forms the sheath of the fibers while the polyester material forms the core. The through-air bonded carded web comprises about 50 weight percent of 3 denier fibers and about 50 weight percent of 10 denier fibers. The 3 denier fibers have a length of about 1.5 inches and the 10 denier fibers have a length of about 2 inches. Both the 3 denier and 10 denier fibers are commercially available from BASF under the trade designation Merge-B1053 (3 denier) and Merge-B1036 (10 denier). The carded web has a random fiber orientation. The humidity transfer material has a basis weight of about 160 g/m$^2$, a bulk thickness of about 0.5 cm (measured under a pressure of 0.207 kPa), and a density of 0.030 g/cm$^3$. This humidity transfer material has a wet compression recovery of 87 percent, a wicking index of 0.20 grams, and a moisture retention index of 14 grams.

Sample C

This humidity transfer material comprised a through-air bonded carded web formed from polyester fibers and polyethylene/polypropylene side-by-side bicomponent fibers. The polyester fibers have a denier of about 6 d, a length of about 2 inches, and are commercially available from Hoechst Celanese Corporation, Charlotte, N.C. under the trade designation Type 295. The polyethylene/polypropylene side-by-side bicomponent fibers have a length of about 1.5 inches, a denier of about 1.7 d, and are commercially available from Chisso under the trade designation Chisso ES. The through-air bonded carded web comprises about 60 weight percent of the polyester fibers and about 40 weight percent of the polyethylene/polypropylene sheath core fibers. The humidity transfer material has a basis weight of about 160 g/m$^2$, a bulk thickness of about 0.5 cm (measured under a load of 0.207 kPa), and a density of about 0.045 g/cm$^3$. This humidity transfer material has a wet compression recovery of 74 percent, a wicking index of 0.53 gram, and a moisture retention index of 5.0 grams.

Disposable diapers employing the three humidity transfer materials described above are produced. The diapers generally correspond in size and construction to a commercially available diaper available from Kimberly-Clark Corporation under the trade designation Huggies™ Supreme, Step 4. The diaper has generally the configuration illustrated in FIG. 2. The diapers comprise a liquid-permeable topsheet layer, a liquid- and vapor-impermeable backsheet layer, and an absorbent body located between the liquid-permeable topsheet layer and the backsheet layer. The topsheet layer comprises spunbond polypropylene fabric having a basis weight of 20 g/m$^2$, which fabric is treated with 0.25–0.28 weight percent of a surfactant commercially available from Rohm and Haas under the trade designation Triton™ X-102. The liquid- and vapor-impermeable backsheet layer comprises a 0.6 mil polyolefin film having thermally bonded thereto a 20 g/m$^2$ polypropylene spunbond material. The backsheet material is that used on the HUGGIES™ Supreme diaper commercially available from Kimberly-Clark Corporation. The absorbent body is an airlaid superabsorbent/wood pulp fluff mixture comprising approximately 50 weight percent of superabsorbent material. The wood pulp fluff is the bleached softwood commercially available from Kimberly-Clark Corporation under the designation CR-54. The superabsorbent material is a polyacrylate material commercially available from Hoechst Celanese Corporation under the trade designation IM-5000. The absorbent core has a basis weight of about 650 g/m$^2$.

As illustrated in FIG. 2, the absorbent core is configured to define a humidity transfer area in the front waistband section of the diaper. The humidity transfer area was formed by positioning the absorbent core so that an area of approximately 58.1 cm$^2$ in the front waistband section of the diaper was not overlaid by the absorbent core. A vapor-permeable panel 56 is formed in the backsheet layer by cutting. The vapor-permeable panel started approximately 2.54 cm from the front of the diaper and extended longitudinally along the diaper approximately 3.8 cm. The width of the vapor-permeable panel 56 was approximately 15.2 cm with the vapor-permeable panel being generally centered in the transverse direction of the diaper. A vapor-permeable laminate covers the vapor-permeable panel 56. The vapor-permeable laminate is generally liquid impermeable and covers the vapor-permeable panel 56 by being attached to the outer surface of the diaper. The liquid-impermeable, vapor-permeable laminate comprises a spunbond/meltblown/spunbond material. The spunbond layers have a basis weight of about 17 grams per square meter and are formed from polypropylene fibers having a denier of about 2.0–2.5 d. The meltblown material is formed from polypropylene fibers having a diameter of about 2–5 microns, with the meltblown layer having a basis weight of about 17 grams per square meter. The liquid-impermeable, vapor-permeable laminate has a length of about 6.4 centimeters and a width of about 17.8 centimeters. The liquid-impermeable, vapor-permeable laminate has a water vapor transmission rate of approximately 4000 g/m$^2$/24 hours. A loop material is attached to the outer surface of the SMS material by a one-half inch perimeter seal formed by two-sided adhesive tape. The loop material is a woven loop fabric commercially available from Guilford Mills under the trade designation Guilford loop 34285. One of the above-described humidity transfer materials was positioned as illustrated in FIG. 2 to overlay the humidity transfer area, the vapor-permeable panel 56, and to extend over the absorbent body into the intermediate section of the diaper. The humidity transfer material was approximately 10.2 cm wide and approximately 25.4 cm in length. Waist and leg portions of the diaper were elasticized. Leakage control flaps were attached to the liquid-pervious topsheet. The diaper also included hook fastening tabs 50 adapted to engage with the loop surface of the liquid-impermeable, vapor-permeable laminate covering the vapor-permeable panel 56.

A control diaper was used for comparison. The control diaper was a handmade version of the HUGGIES™ Supreme diaper commercially available from Kimberly-Clark Corporation. The handmade versions of the diaper were essentially identical to the commercial versions of the Supreme diaper and were sized to correspond to a Step 4 diaper.

Diapers formed as described above and employing one of the humidity transfer materials designated as Examples A, B, or C above, and the control diaper were tested to determine the mean skin hydration value. The results of this testing are set forth in Table 1.

TABLE 1

| Humidity Transfer Material | Wet Compression[1] Recovery | Wicking Index[2] | Moisture Retention Index[3] | Mean[4] SHV | % Reduction vs. Control |
|---|---|---|---|---|---|
| A | 97% | 0.02 | 0.15 | 2.4 | 55 |
| B | 87% | 0.20 | 14.0 | 2.3 | 57 |
| C | 74% | 0.53 | 5.0 | 3.7 | 30 |
| Control Diaper | — | — | — | 5.3 | N/A |

[1]Of Humidity Transfer Material In percent
[2]Of Humidity Transfer Material In grams
[3]Of Humidity Transfer Material In grams using 225 milliliter loading
[4]In grams/m$^2$/hour based on testing on 12 infants (N = 12)

As can be seen from the above Table 1, the present invention allows for a dramatic reduction in the mean skin hydration value compared to the control conventional diaper.

Example 2

A diaper having the general configuration illustrated in FIG. 1 was formed as described above in connection with Example 1 with the diaper employing Sample B as a humidity transfer material. The diaper was the same as described in Example 1 with the exception that the liquid- and the vapor-impermeable laminate material employed as the backsheet in Example 1 was replaced with a liquid-impermeable, vapor-permeable microporous polymeric film. The microporous polymeric film has a water vapor transmission rate of approximately 3700 g/m$^2$/24 hours. Thus, the diaper of this example has a substantially liquid-impermeable but vapor-permeable backsheet layer. A vapor-permeable panel was formed in this backsheet as in Example 1. The diaper so formed employing the humidity transfer material of Sample B in Example 1 was found to have a mean net skin hydration value of about 3.0 g/m$^2$/hour (using a 225 milliliter loading, tested on 12 infants, (N-12)) which represented a 72 percent reduction in skin hydration compared to the control diaper of Example 1. While the control diaper had the same configuration as that used in Example 1, the control diaper was used, in this Example, with a set of babies different than those used in connection with Example 1. Accordingly, the mean skin hydration value for the control diaper differs from that reported in Table 1.

Comparative Example 1

A diaper similar to that formed in Example 1 is prepared with the exception that the absorbent body extends to the end of the humidity transfer material located in the front waistband section of the diaper. That is, the absorbent body is coterminous with the humidity transfer material in the front waistband section of the diaper so that no humidity transfer area is defined within the diaper. This diaper exhibited a mean net skin hydration value of about 9.4 g/m$^2$ per hour (using a 150 milliliter loading tested on 12 infants (N=12)). This represented no reduction in skin hydration compared to the control diaper of Example 1.

Having thus described the invention in rather full detail, it will be readily apparent to a person of ordinary skill that various changes and modifications can be made without departing from the spirit of the invention. All of such changes and modifications are contemplated as being within the scope of the present invention as defined by the subjoined claims.

We claim:

1. An absorbent article, which generally delimits a front waistband section, a rear waistband section and an intermediate section which interconnects said front and rear waistband sections, said article comprising:
    a vapor-permeable backsheet layer having a length;
    a liquid-permeable topsheet layer positioned in facing relation with said backsheet layer;
    an absorbent body located between said backsheet layer and said topsheet layer and having a length which is less than the length of said backsheet layer, said absorbent body overlaying at least a portion of said backsheet layer;
    a humidity transfer area formed by positioning said absorbent body such that an area of at least about 5.0 square centimeters of said backsheet in at least one waistband section of said article is not overlaid by said absorbent body; and
    a humidity transfer material located between said topsheet layer and said backsheet layer, said humidity transfer material overlaying said humidity transfer area and extending over said absorbent body and into said intermediate section of said article;
    wherein said absorbent body has a water vapor transmission rate value, when wet, which is less than the water vapor transmission rate value of said backsheet.

2. An absorbent article according to claim 1 wherein said absorbent body has a density of from about 0.03 to about 0.4 gram per cubic centimeter.

3. An absorbent article according to claim 1 wherein said absorbent body has a density of from about 0.05 to about 0.2 gram per cubic centimeter.

4. An absorbent article according to claim 1 wherein said humidity transfer area has an area of at least about 22.0 square centimeters.

5. An absorbent article according to claim 1 wherein said humidity transfer area has an area of from about 45 to about 90 square centimeters.

6. An absorbent article according to claim 1 wherein said humidity transfer material has a wet compression recovery of at least about 87 percent.

7. An absorbent article according to claim 1 wherein said humidity transfer material has a wet compression recovery of at least about 97 percent.

8. An absorbent article according to claim 1 wherein said humidity transfer material is formed from a material selected from the group consisting of nonwoven fibrous webs and porous foams.

9. An absorbent article according to claim 1 wherein said humidity transfer material has a bulk thickness (at 0.207 kPa) within the range of about 0.2 to about 0.7 centimeter.

10. An absorbent article according to claim 1 wherein said humidity transfer area is formed in the front waistband section of said backsheet layer.

11. An absorbent article according to claim 1 wherein said humidity transfer area is formed in the rear waistband section of said backsheet layer.

12. An absorbent article according to claim 1 wherein said humidity transfer area is formed in each of the front waistband section and the rear waistband section of said backsheet layer.

13. An absorbent article according to claim 1 wherein said humidity transfer material has a Moisture Retention Index of not more than about 40 grams.

14. An absorbent article according to claim 13 wherein said humidity transfer material has a Moisture Retention Index of not more than about 30 grams.

15. An absorbent article according to claim 1 wherein said humidity transfer material has a Wicking Index of not more than about 0.5 gram.

16. An absorbent article according to claim 15 wherein said humidity transfer material has a Wicking Index of not more than about 0.2 gram.

17. An absorbent article according to claim 1 wherein said humidity transfer material has a basis weight of from about 120 to about 160 grams per square meter.

18. An absorbent article according to claim 1 further comprising an absorbent insert positioned between said humidity transfer material and said topsheet layer and overlaying said humidity transfer area.

19. An absorbent article according to claim 1 wherein said vapor-permeable backsheet has a water vapor transmission rate value of at least about 1000 g/sq.m/24 hr.

20. An absorbent article according to claim 19 wherein said humidity transfer material has a wet compression recovery of at least about 74 percent.

21. An absorbent article according to claim 1 wherein said vapor-permeable backsheet has a water vapor transmission rate value of at least about 2000 g/sq.m/24 hr.

22. An absorbent article according to claim 21 wherein said humidity transfer material has a wet compression recovery of at least about 74 percent.

23. An absorbent article according to claim 1 wherein said vapor-permeable backsheet has a water vapor transmission rate value of at least about 3000 g/sq.m/24 hr.

24. An absorbent article according to claim 23 wherein said humidity transfer material has a wet compression recovery of at least about 74 percent.

25. An absorbent article according to claim 1 wherein said humidity transfer material has a wet compression recovery of at least about 74 percent.

26. An absorbent article, which generally delimits a front waistband section, a rear waistband section and an intermediate section which interconnects said front and rear waistband sections, said article comprising:

a vapor-permeable backsheet layer having a length;

a liquid-permeable topsheet layer positioned in facing relation with said backsheet layer;

an absorbent body located between said backsheet layer and said topsheet layer and having a length which is less than the length of said backsheet layer, said absorbent body overlaying at least a portion of said backsheet layer;

a humidity transfer area formed by positioning said absorbent body such that an area of at least about 5.0 square centimeters of said backsheet in at least one waistband section of said article is not overlaid by said absorbent body; and a humidity transfer material located between said topsheet layer and said backsheet layer, said humidity transfer material overlaying said humidity transfer area and extending over said absorbent body and into said intermediate section of said article; and wherein said humidity transfer material has a water vapor transmission rate value, when wet, which is equal to or greater than said backsheet.

27. An absorbent article according to claim 26 wherein said vapor-permeable backsheet has a water vapor transmission rate value of at least about 1000 g/sq.m/24 hr.

28. An absorbent article according to claim 27 wherein said humidity transfer material has a wet compression recovery of at least about 74 percent.

29. An absorbent article according to claim 26 wherein said vapor-permeable backsheet has a water vapor transmission rate value of at least about 2000 g/sq.m/24 hr.

30. An absorbent article according to claim 29 wherein said humidity transfer material has a wet compression recovery of at least about 74 percent.

31. An absorbent article according to claim 26 wherein said vapor-permeable backsheet has a water vapor transmission rate value of at least about 3000 g/sq.m/24 hr.

32. An absorbent article according to claim 31 wherein said humidity transfer material has a wet compression recovery of at least about 74 percent.

33. An absorbent article according to claim 26 wherein said humidity transfer material has a wet compression recovery of at least about 74 percent.

* * * * *